US006297429B1

(12) United States Patent
Takatsuji et al.

(10) Patent No.: US 6,297,429 B1
(45) Date of Patent: Oct. 2, 2001

(54) GENE FOR TRANSCRIPTION FACTOR CAPABLE OF ALTERING CHARACTERS OF A PLANT AND USE THEREOF

(75) Inventors: Hiroshi Takatsuji, Tsukuba; Hitoshi Nakagawa, Inashiki-gun, both of (JP)

(73) Assignees: Director General of National Institute of Agrobiological Resources; Ministry of Agriculture, Forestry and Fisheries, both of Ibaragi (JP)

( * ) Notice: Subject to any disclaimer, the term of this patent is extended or adjusted under 35 U.S.C. 154(b) by 0 days.

(21) Appl. No.: 09/156,579

(22) Filed: Sep. 18, 1998

(30) Foreign Application Priority Data

Mar. 16, 1998 (JP) .................................................. 10-065921

(51) Int. Cl.[7] ........................... C12N 15/29; C12N 15/82; C12N 15/90; A01H 5/00
(52) U.S. Cl. ....................... 800/290; 435/468; 435/320.1; 536/23.6; 800/298; 800/317; 800/323.1
(58) Field of Search ................................. 435/691, 320.1, 435/468; 536/23.6; 800/278, 290, 295, 298, 317, 323.1

(56) References Cited

FOREIGN PATENT DOCUMENTS

WO 90/12084    10/1990  (WO) ............................. C12N/15/00

OTHER PUBLICATIONS van der Krol et al, Nature, vol. 333, pp. 866–869, 1988.*
Kubo, K. et al., "CyS2/His2 zinc–finger protein family of petunia: evolution and general mechanism of target–sequence recognition," *Nuc. Acids Res.*, vol. 26, No. 2, pp. 608–615 (1998).

Sakai, H. et al. "Role of SUPERMAN in maintaining Arabidopsis floral whorl boundaries." *Nature* 378:199–203 (1995).

Tangue, B.W. and Goodman, H.M. "Characterization of a family of Arabidopsis zinc finger protein cDNAs." *Plant mol. Biol.* 28:267–279 (1995). (Abstract and EMBL sequence information enclosed.)

Takatsuji Hiroshi. "Transcription Factors Controlling Floral Organ Development." *Cell Technology. Plant Technology Series*. Shujunsha, Japan, pp. 96–106.

Takatsuji, Hiroshi. *The IDEN*, vol. 51, No. 4, pp. 34–38 (1997).

* cited by examiner

*Primary Examiner*—Gary Benzion
*Assistant Examiner*—Ashwin D. Mehta
(74) *Attorney, Agent, or Firm*—Townsend and Townsend and Crew LLP

(57) ABSTRACT

A gene encoding DNA which is selected from a) or b): a) DNA having a nucleotide sequence from the 90th position to the 728th position of a nucleotide sequence represented in SEQ ID NO: 1 of Sequence Listing; or b) DNA which hybridizes to DNA of a) under stringent conditions, and encodes a transcription factor capable of altering characters of a plant.

16 Claims, 8 Drawing Sheets

(5 of 8 Drawing Sheet(s) Filed in Color)

| | | | | |
|---|---|---|---|---|
| TCTACAAGGC | AATAACAAGT | TATAGTATCA | TCTTTCTTTT | ATTACCTTTA |
| TAGAACTATC | ATTTTTCCAC | CGTTGACTCT | CTCTCTCTAA | TGGAAACTAG |
| | | | M | E T S |
| TAAAAATCAG | CCGTCTGTCT | CAGAAAATGT | TGATCAGCAG | AAAGTAGATA |
| K N Q | P S V S | E N V | D Q Q | K V D N |
| ACTCTTCTTC | AGATGAACAA | CAAATTTCAA | TTATCCAAAG | CAGCCATACT |
| S S S | D E Q | Q I S I | I Q S | S H T |
| ACTAAATCCT | ATGAGTGCAA | CTTTTGTAAA | AGAGGTTTTT | CTAACGCACA |
| T K S Y | E C N | F C K | R G F S | N A Q |
| AGCACTTGGT | GGCCACATGA | ATATCCATCG | TAAGGACAAG | GCCAAACTCA |
| A L G | G H M N | I H R | K D K | A K L K |
| AAAAACAAAA | GCAGCATCAA | CGACAACAAA | AACCTACCTC | GGTTTCCAAA |
| K Q K | Q H Q | R Q Q K | P T S | V S K |
| GAAACCAACA | TGGCTCACAA | TATCTTGCTA | GCGGATGATT | CTAACATCCC |
| E T N M | A H N | I L L | A D D S | N I P |
| TACCACAATC | CCCTTTTTC | CTTCTCTTAC | ATCACCAAAC | ACATCCAACC |
| T T I | P F F P | S L T | S P N | T S N P |
| CTTTAGGGTT | CGTGTCTTCT | TGCACTACTG | CAGACACCGT | CGGGCAAAGA |
| L G F | V S S | C T T A | D T V | G Q R |
| CAGATTCAAG | ATCTAAACTT | AGTCATGGGT | TCAACTCTTA | ACGTTCTCAG |
| Q I Q D | L N L | V M G | S T L N | V L R |
| AATGAATAGT | GTTGAAGCGG | GTTCTGTTGA | TTCACGTGAA | AATAGATTGC |
| M N S | V E A G | S V D | S R E | N R L P |
| CGGCTAGAAA | TCAAGAAACT | ACACCATTTT | ACGCGGAATT | GGACCTTGAG |
| A R N | Q E T | T P F Y | A E L | D L E |
| CTGCGATTAG | GTCATGAGCC | TGCACCTTCC | ACGGATATAT | CATCAGCTAA |
| L R L G | H E P | A P S | T D I S | S A N |
| TTCGGGTTTA | GGCACAAGAA | AGTTCTTATG | ATTTATTGGT | ACTATTGCTG |
| S G L | G T R K | F L | | |
| CTAATGCTT | TTTCTTTTA | CTACTGTTTA | GGGTTTTTTT | GTGACTATGA |
| TACTACTTTT | GCTACATCTG | AATTGTCTTG | AACTCTTTTA | TTCAGAGTTC |
| TTGGATTTG | CTTTGCTTGT | TTTAATCTGG | CTCTAGA | |

FIG. 1

SEQUENCE LISTING

```
<160> NUMBER OF SEQ ID NOS: 20

<210> SEQ ID NO 1
<211> LENGTH: 887
<212> TYPE: DNA
<213> ORGANISM: Petunia x hybrida
<220> FEATURE:
<221> NAME/KEY: CDS
<222> LOCATION: (90)..(731)
<223> OTHER INFORMATION: PetSPL3

<400> SEQUENCE: 1
tctacaaggc aataacaagt tatagtatca tctttctttt attacctttta tagaactatc      60 atttttccac cgttgactct ctctctcta atg gaa act agt aaa aat cag ccg       113
                                Met Glu Thr Ser Lys Asn Gln Pro
                                  1               5 tct gtc tca gaa aat gtt gat cag cag aaa gta gat aac tct tct tca       161
Ser Val Ser Glu Asn Val Asp Gln Gln Lys Val Asp Asn Ser Ser Ser
       10                  15                  20 gat gaa caa caa att tca att atc caa agc agc cat act act aaa tcc       209
Asp Glu Gln Gln Ile Ser Ile Ile Gln Ser Ser His Thr Thr Lys Ser
 25                  30                  35                  40 tat gag tgc aac ttt tgt aaa aga ggt ttt tct aac gca caa gca ctt       257
Tyr Glu Cys Asn Phe Cys Lys Arg Gly Phe Ser Asn Ala Gln Ala Leu
                 45                  50                  55 ggt ggc cac atg aat atc cat cgt aag gac aag gcc aaa ctc aaa aaa       305
Gly Gly His Met Asn Ile His Arg Lys Asp Lys Ala Lys Leu Lys Lys
             60                  65                  70 caa aag cag cat caa cga caa caa aaa cct acc tcg gtt tcc aaa gaa       353
Gln Lys Gln His Gln Arg Gln Gln Lys Pro Thr Ser Val Ser Lys Glu
         75                  80                  85 acc aac atg gct cac aat atc ttg cta gcg gat gat tct aac atc cct       401
Thr Asn Met Ala His Asn Ile Leu Leu Ala Asp Asp Ser Asn Ile Pro
     90                  95                 100 acc aca atc ccc ttt ttt cct tct ctt aca tca cca aac aca tcc aac       449
Thr Thr Ile Pro Phe Phe Pro Ser Leu Thr Ser Pro Asn Thr Ser Asn
105                 110                 115                 120 cct tta ggg ttc gtg tct tct tgc act act gca gac acc gtc ggg caa       497
Pro Leu Gly Phe Val Ser Ser Cys Thr Thr Ala Asp Thr Val Gly Gln
                125                 130                 135 aga cag att caa gat cta aac tta gtc atg ggt tca act ctt aac gtt       545
Arg Gln Ile Gln Asp Leu Asn Leu Val Met Gly Ser Thr Leu Asn Val
            140                 145                 150 ctc aga atg aat agt gtt gaa gcg ggt tct gtt gat tca cgt gaa aat       593
```

-continued

```
                Leu Arg Met Asn Ser Val Glu Ala Gly Ser Val Asp Ser Arg Glu Asn
                            155                 160                 165 aga ttg ccg gct aga aat caa gaa act aca cca ttt tac gcg aa ttg              641
Arg Leu Pro Ala Arg Asn Gln Glu Thr Thr Pro Phe Tyr Ala Glu Leu
        170                 175                 180 gac ctt gag ctg cga tta ggt cat gag cct gca cct tcc acg gat ata              689
Asp Leu Glu Leu Arg Leu Gly His Glu Pro Ala Pro Ser Thr Asp Ile
185                 190                 195                 200 tca tca gct aat tcg ggt tta ggc aca aga aag ttc tta tgatttattg              738
Ser Ser Ala Asn Ser Gly Leu Gly Thr Arg Lys Phe Leu
                205                 210 gtactattgc tgctaaatgc tttttctttt tactactgtt tagggttttt ttgtgactat           798
gatactactt ttgctacatc tgaattgtct tgaactcttt tattcagagt tcttggattt           858
tgctttgctt gttttaatct ggctctaga                                             887
```

<210> SEQ ID NO 2
<211> LENGTH: 213
<212> TYPE: PRT
<213> ORGANISM: Petunia x hybrida var. Mitchell

<400> SEQUENCE: 2

```
Met Glu Thr Ser Lys Asn Gln Pro Ser Val Ser Glu Asn Val Asp Gln
1               5                   10                  15

Gln Lys Val Asp Asn Ser Ser Asp Glu Gln Gln Ile Ser Ile Ile
                20                  25                  30

Gln Ser Ser His Thr Thr Lys Ser Tyr Glu Cys Asn Phe Cys Lys Arg
            35                  40                  45

Gly Phe Ser Asn Ala Gln Ala Leu Gly Gly His Met Asn Ile His Arg
        50                  55                  60

Lys Asp Lys Ala Lys Leu Lys Lys Gln Lys Gln His Gln Arg Gln Gln
65                  70                  75                  80

Lys Pro Thr Ser Val Ser Lys Glu Thr Asn Met Ala His Asn Ile Leu
                85                  90                  95

Leu Ala Asp Asp Ser Asn Ile Pro Thr Thr Ile Pro Phe Phe Pro Ser
            100                 105                 110

Leu Thr Ser Pro Asn Thr Ser Asn Pro Leu Gly Phe Val Ser Ser Cys
        115                 120                 125

Thr Thr Ala Asp Thr Val Gly Gln Arg Gln Ile Gln Asp Leu Asn Leu
    130                 135                 140

Val Met Gly Ser Thr Leu Asn Val Leu Arg Met Asn Ser Val Glu Ala
145                 150                 155                 160

Gly Ser Val Asp Ser Arg Glu Asn Arg Leu Pro Ala Arg Asn Gln Glu
                165                 170                 175

Thr Thr Pro Phe Tyr Ala Glu Leu Asp Leu Glu Leu Arg Leu Gly His
            180                 185                 190

Glu Pro Ala Pro Ser Thr Asp Ile Ser Ser Ala Asn Ser Gly Leu Gly
        195                 200                 205

Thr Arg Lys Phe Leu
    210
```

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:primer 1
<221> NAME/KEY: modified_base

```
<222> LOCATION: (6)
<223> OTHER INFORMATION: i
<221> NAME/KEY: modified_base
<222> LOCATION: (9)
<223> OTHER INFORMATION: i
<221> NAME/KEY: modified_base
<222> LOCATION: (12)
<223> OTHER INFORMATION: i
<221> NAME/KEY: modified_base
<222> LOCATION: (15)
<223> OTHER INFORMATION: i

<400> SEQUENCE: 3
cargcnytng gnggncay                                                      18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:primer 2
<221> NAME/KEY: modified_base
<222> LOCATION: (3)
<223> OTHER INFORMATION: i
<221> NAME/KEY: modified_base
<222> LOCATION: (6)
<223> OTHER INFORMATION: i
<221> NAME/KEY: modified_base
<222> LOCATION: (9)
<223> OTHER INFORMATION: i

<400> SEQUENCE: 4
ytnggnggnc ayatgaay                                                      18

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:primer 3
<221> NAME/KEY: modified_base
<222> LOCATION: (3)
<223> OTHER INFORMATION: i
<221> NAME/KEY: modified_base
<222> LOCATION: (6)
<223> OTHER INFORMATION: i
<221> NAME/KEY: modified_base
<222> LOCATION: (12)
<223> OTHER INFORMATION: i

<400> SEQUENCE: 5
arncknaryt cnarrtc                                                       17

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 6
actggatccc attagagaga gagag                                              25

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:reverse primer

<400> SEQUENCE: 7
```
ggaaacagct atgaccatg                                                         19

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:amino acid
      sequence corresponding to primer 1

<400> SEQUENCE: 8

Gln Ala Leu Gly Gly His
  1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:amino acid
      sequence corresponding to primer 2

<400> SEQUENCE: 9

Leu Gly Gly His Met Asn
  1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:amino acid
      sequence corresponding to primer 3

<400> SEQUENCE: 10

Asp Leu Glu Leu Arg Leu
  1               5

<210> SEQ ID NO 11
<211> LENGTH: 43
<212> TYPE: PRT
<213> ORGANISM: Artificial Sequence
<220> FEATURE:
<223> OTHER INFORMATION: Description of Artificial Sequence:zinc-finger
      motif of SUPERMAN

<400> SEQUENCE: 11

Ser Tyr Thr Cys Ser Phe Cys Lys Arg Glu Phe Arg Ser Ala Gln Ala
  1               5                  10                  15

Leu Gly Gly His Met Asn Val His Arg Arg Asp Arg Ala Arg Leu Arg
             20                  25                  30

Leu Gln Gln Ser Pro Ser Ser Ser Thr Pro
         35                  40

<210> SEQ ID NO 12
<211> LENGTH: 42
<212> TYPE: PRT
<213> ORGANISM: Artificial Sequence
<220> FEATURE:
<223> OTHER INFORMATION: Description of Artificial Sequence:zinc-finger
      motif of PetSPL1

<400> SEQUENCE: 12

Ser Tyr Thr Cys Ser Phe Cys Lys Arg Glu Phe Arg Ser Ala Gln Ala
  1               5                  10                  15

Leu Gly Gly His Met Asn Val His Arg Arg Asp Arg Ala Arg Leu Arg
            20                  25                  30

Leu Gln Ser Pro Pro Arg Glu Asn Gly Thr
        35                  40

<210> SEQ ID NO 13
<211> LENGTH: 41
<212> TYPE: PRT
<213> ORGANISM: Artificial Sequence
<220> FEATURE:
<223> OTHER INFORMATION: Description of Artificial Sequence:zinc-finger
      motif of PetSPL2

<400> SEQUENCE: 13

Ser Tyr Thr Cys Ser Phe Cys Lys Arg Glu Phe Arg Ser Ala Gln Ala
  1               5                  10                  15

Leu Gly Gly His Met Asn Val His Arg Arg Asp Arg Ala Ile Leu Arg
            20                  25                  30

Gln Ser Pro Pro Arg Asp Ile Asn Arg
        35                  40

<210> SEQ ID NO 14
<211> LENGTH: 43
<212> TYPE: PRT
<213> ORGANISM: Artificial Sequence
<220> FEATURE:
<223> OTHER INFORMATION: Description of Artificial Sequence:zinc-finger
      motif of PetSPL3

<400> SEQUENCE: 14

Ser Tyr Glu Cys Asn Phe Cys Lys Arg Gly Phe Ser Asn Ala Gln Ala
  1               5                  10                  15

Leu Gly Gly His Met Asn Ile His Arg Lys Asp Lys Ala Lys Leu Lys
            20                  25                  30

Lys Gln Lys Gln His Gln Arg Gln Gln Lys Pro
        35                  40

<210> SEQ ID NO 15
<211> LENGTH: 43
<212> TYPE: PRT
<213> ORGANISM: Artificial Sequence
<220> FEATURE:
<223> OTHER INFORMATION: Description of Artificial Sequence:zinc-finger
      motif of PetSPL4

<400> SEQUENCE: 15

Phe Tyr Arg Cys Ser Phe Cys Lys Arg Gly Phe Ser Asn Ala Gln Ala
  1               5                  10                  15

Leu Gly Gly His Met Asn Ile His Arg Lys Asp Arg Ala Lys Leu Arg
            20                  25                  30

Glu Ile Ser Thr Asp Asn Leu Asn Ile Asp Gln
        35                  40

<210> SEQ ID NO 16
<211> LENGTH: 33
<212> TYPE: PRT
<213> ORGANISM: Artificial Sequence
<220> FEATURE:
<223> OTHER INFORMATION: Description of Artificial Sequence:C-terminal
      hydrophobic region of SUPERMAN

<400> SEQUENCE: 16

Ile Leu Arg Asn Asp Glu Ile Ile Ser Leu Glu Leu Glu Ile Gly Leu
  1               5                  10                  15

Ile Asn Glu Ser Glu Gln Asp Leu Asp Leu Glu Leu Arg Leu Gly Phe
            20                  25                  30

Ala

<210> SEQ ID NO 17
<211> LENGTH: 33
<212> TYPE: PRT
<213> ORGANISM: Artificial Sequence
<220> FEATURE:
<223> OTHER INFORMATION: Description of Artificial Sequence:C-terminal
      hydrophobic region of PetSPL1

<400> SEQUENCE: 17

Leu Met Lys Arg Ser Glu Phe Leu Arg Leu Glu Leu Gly Ile Gly Met
 1               5                  10                  15

Ile Asn Glu Ser Lys Glu Asp Leu Asp Leu Glu Leu Arg Leu Gly Tyr
            20                  25                  30

Thr

<210> SEQ ID NO 18
<211> LENGTH: 33
<212> TYPE: PRT
<213> ORGANISM: Artificial Sequence
<220> FEATURE:
<223> OTHER INFORMATION: Description of Artificial Sequence:C-terminal
      hydrophobic region of PetSPL2

<400> SEQUENCE: 18

Val Ile Lys Lys Ser Glu Phe Leu Arg Leu Asp Leu Gly Ile Gly Leu
 1               5                  10                  15

Ile Ser Glu Ser Lys Glu Asp Leu Asp Leu Glu Leu Arg Leu Gly Ser
            20                  25                  30

Thr

<210> SEQ ID NO 19
<211> LENGTH: 33
<212> TYPE: PRT
<213> ORGANISM: Artificial Sequence
<220> FEATURE:
<223> OTHER INFORMATION: Description of Artificial Sequence:C-terminal
      hydrophobic region of PetSPL3

<400> SEQUENCE: 19

Gly Ser Val Asp Ser Arg Glu Asn Arg Leu Pro Ala Arg Asn Gln Glu
 1               5                  10                  15

Thr Thr Pro Phe Tyr Ala Glu Leu Asp Leu Glu Leu Arg Leu Gly His
            20                  25                  30

Glu

<210> SEQ ID NO 20
<211> LENGTH: 33
<212> TYPE: PRT
<213> ORGANISM: Artificial Sequence
<220> FEATURE:
<223> OTHER INFORMATION: Description of Artificial Sequence:C-terminal
      hydrophobic region of PetSPL4

<400> SEQUENCE: 20

```
Cys Gly Thr Leu Asp Glu Lys Pro Lys Arg Gln Ala Glu Asn Asn Asp
 1               5              10                   15
Met Gln Gln Asp Asp Ser Lys Leu Asp Leu Glu Leu Arg Leu Gly Pro
            20              25                  30
Asp
```

GENE FOR TRANSCRIPTION FACTOR CAPABLE OF ALTERING CHARACTERS OF A PLANT AND USE THEREOF

BACKGROUND OF THE INVENTION

1. Field of the Invention

The present invention relates to a gene encoding a transcription factor capable of altering characters of a plant and its use. More particularly, the present invention relates to the PetSPL3 gene which is a novel gene derived from *Petunia hybrida*, genes related thereto, and the use thereof.

2. Description of the Related Art

In order to clarify regulatory mechanisms controlling the characters of a plant, for example, morphogenesis of a flower, molecular biological and molecular geneticical studies have been conducted using *Arabidopsis thaliana, Antirrhinum majus,* and *Petunia hybrida*. In particular, *Petunia hybrida* is preferably used as a subject of studies for the following reasons: high value as a horticultural plant: the presence of various species; ease of transformation; ease to observe due to its large flower, and accumulation of genetical findings (H. Takatsuji, "Molecular mechanism for determining a shape of a plant", Cell Technology, Plant Cell Technology Series (SHUJUNSHA), pp. 96–106).

Genes which cause mutation have been isolated from mutants in which floral organs of the above-mentioned plant is altered. As a result, it is becoming clear that transcription factors play important roles in differentiation and morphogenesis of a flower. For example, SUPERMAN of *Arabidopsis thaliana* is a transcription factor having a zinc finger motif as a DNA binding domain. It is known that, in SUPERMAN mutant, the number of stamens are remarkably increased, and pistils are defective (THE IDEN, April, 1997 (Vol. 51, No. 4), pp. 34–38).

For understanding the mechanism for the control of characters of a plant, it is important to identify a novel transcription factor which is involved in the control. A gene for a transcription factor which controls morphogenesis of a flower may be introduced into a plant by using gene engineering procedure. It is possible to obtain a plant, using gene introduction, having a flower with novel characters which has not been obtained or is not likely to be obtained by a conventional breeding. It is considered that a plant with such novel characters is horticulturally valuable.

SUMMARY OF THE INVENTION

A gene of the present invention has DNA which is selected from a) or b): a) DNA having a nucleotide sequence from the 90th position to the 728th position of a nucleotide sequence represented in SEQ ID NO: 1 of Sequence Listing; or b) DNA which hybridizes to DNA of a) under stringent conditions, and encodes a transcription factor capable of altering characters of a plant.

A gene of the present invention encodes a transcription factor which is selected from i) or ii):

i) a transcription factor having an amino acid sequence from the 1st position to the 213rd position of an amino acid sequence represented in SEQ ID NO: 2; or ii) a transcription factor having an amino acid sequence in which one or more amino acids of i) are subjected to deletion, substitution, or addition, and being capable of altering characters of a plant.

In one embodiment of the present invention, the characters of a plant include one selected from the group consisting of morphology of a flower, color of a flower, a size of a plant, and the number of branches.

A method for producing a transgenic plant of the present invention includes the steps of: introducing a plant cell with the above-mentioned gene: and regenerating a plant body from the plant cell with the introduced-gene.

In one embodiment of the present invention, the plant belongs to dicotyledon.

In another embodiment of the present invention, the plant belongs to Solanaceae.

In another embodiment of the present invention, the plant belongs to Petunia.

In another embodiment of the present invention, the gene is incorporated into a plant expression vector.

A transgenic plant of the present invention is produced by the above-mentioned method.

Thus, the invention described herein makes possible the advantages of (1) providing a gene encoding a transcription factor capable of altering characters of a plant; (2) providing a method for producing a plant with its character altered by introduction of the gene; and (3) providing a transgenic plant.

These and other advantages of the present invention will become apparent to those skilled in the art upon reading and understanding the following detailed description with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows a nucleotide sequence(SEQ ID NO: 1) of PetSPL3 gene and its deduced amino acid sequence(SEQ ID NO: 2).

DESCRIPTION OF THE PREFERRED EMBODIMENTS

Figure 2A:
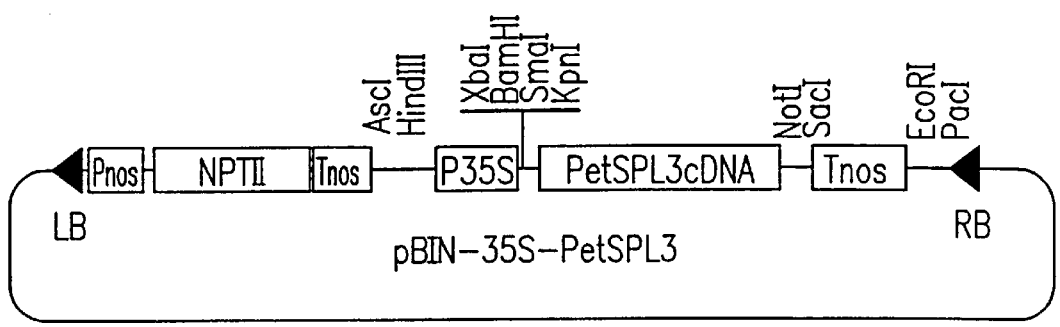
FIG. 2A is a schematic view showing a high expression vector (pBIN-35S-PetSPL3) containing the PetSPL3 gene.

Hereinafter, the present invention will be described in detail.

The term "transcription factor" as used herein refers to a protein which binds to a DNA regulatory region of genes to control the synthesis of mRNA. Some transcription factors are known to have a highly conservative amino acid sequence called zinc finger motif in their DNA binding domains.

A gene of the present invention encodes a transcription factor capable of altering characters of a plant. This gene may have either of the following DNAs:
  a) DNA having a nucleotide sequence from the 90th position to the 728th position of a nucleotide sequence represented in SEQ ID NO: 1 of Sequence Listing; or
  b) DNA which hybridizes to DNA of a) under stringent conditions, and encodes a transcription factor capable of altering characters of a plant.

The gene of the present invention may also have DNA which encodes a transcription factor capable of altering characters of a plant, and has a homology of about 60% or more, preferably about 70% or more, more preferably about 80% or more, and still more preferably about 90% or more, with DNA of a).

Preferably, the gene of the present invention may contain DNA of a).

The gene of the present invention may-also encode either of the following transcription factors:
  i) a transcription factor having an amino acid sequence from the 1st position to the 213rd position of an amino acid sequence represented in SEQ ID NO: 2; or
  ii) a transcription factor having an amino acid sequence in which one or more amino acids of i) are subjected to deletion, substitution, or addition, and being capable of altering characters of a plant.

The number of amino acids subject to deletion, substitution, or addition may be about 130 or less, preferably about 60 or less, more preferably about 30 or less and still more preferably about 20 or less, stll further more preferably 10 or less.

Preferably, the gene of the present invention may encode the transcription factor of i).

The particularly preferred gene in the present invention is PetSPL3 gene. FIG. 1 shows a cDNA sequence (SEQ ID NO: 1) of this gene and its deduced amino acid sequence (SEQ ID NO: 2).

Alterations in "characters of a plant" refer to any changes in at least one of morphology of a plant and color of a plant, more specifically, any changes in at least one of morphology of a flower, color of a flower, a size of a plant, and the number of branches. These changes are evaluated by comparing the characters of a plant obtained by introducing a gene of the present invention with the characters of a plant (wild-type or horticultural type) before introducing the gene.

Alterations in morphology of a flower and/or color of a flower are examples of preferable alterations of plant morphology. (Hereinafter, the term "flower" refers to petals unless otherwise specified.)

Examples of altered morphology of a flower include, but are not limited to, morphology which may be caused by an alteration in a shape of an individual petal (large petals, small petals, sawtooth-shaped petals, round petals, wave-shaped petals, etc.), morphology which may be caused by an alteration in the number of petals (double flower, single flower, etc.), and morphology which may be caused by abnormal development of petals (star-shaped petals, etc.).

Examples of color change of a flower include, but are not limited to, single colors such as white, scarlet red, salmon pink, rose, pink, blue violet, violet, pale violet, sky blue, violet red, and yellowish white, and multi-color patterns of two or more colors (e.g., variegation, spots, marginal variegation, coloring of an outer edge of a petal).

Examples of a changed size of a plant include, but are not limited to, a dwarf and a semi-dwarf. The dwarfism is preferably about ½ or less, more preferably about ⅓ or less of a standard size of the plant before the introduction of the gene. An example of altered branch number includes but is not limited to increased branching.

Changed characters of a plant include preferably morphology caused by an abnormal development of petals, a double color pattern, a dwarf, or increased branching; and more preferably a combination thereof (e.g., a combination of abnormal development of petals and a double color pattern and/or a combination of a dwarf and increased branching). More preferably, changed characters of a plant include morphology of a star shape, coloring of an outer edge of a petal, a dwarf, or increased branching; and more preferably a combination thereof (e.g., a combination of morphology of a star shape and coloring of an outer edge of a petal and/or a combination of a dwarf and increased branching).

The gene of the present invention can be isolated, for example, by performing polymerase chain reaction (PCR) with genomic DNA of a plant as a template, using a pair of degenerated primers corresponding to a conserved region of the amino acid sequence encoded by a gene of a known transcription factor, and screening a genomic library of the same plant, using the amplified DNA fragment thus obtained as a probe. Examples of a pair of primers include a combination of 5'-CARGCNYTNGGNGGNCAY-3' (SEQ ID NO: 3) or 5'-YTNGGNGGNCAYATGAAY-3' (SEQ ID NO: 4) with 5'-ARNCKNARYTCNARRTC-3' (SEQ ID NO: 5) in which N is inosine, R is G or A, Y is C or T, and K is T or G.

PCR can be performed in accordance with the anufacturer's instructions for a commercially available it and instruments, or by a procedure well known to those skilled in the art. A method for producing a gene library, stringent conditions used for hybridization with a probe, and a method for cloning a gene are well known to those skilled in the art. For example, see Maniatis et al., Molecular Cloning, A Laboratory Manual, 2nd Ed., Cold Spring Harbor Laboratory Press, Cold Spring Harbor, N.Y. (1989).

A nucleotide sequence of the gene thus obtained can be determined by a nucleotide sequence analysis method known in the art or by a commercially available automatic sequencer.

The gene of the present invention is not limited to those isolated from native genome, but may include synthetic polynucleotides. Synthetic polynucleotides can be obtained, for example, by modifying a sequenced gene as described above using a procedure well known to those skilled in the art.

The gene of the present invention can be ligated to an appropriate plant expression vector by a method well known to those skilled in the art and introduced into a plant cell by a known gene recombination technique. The introduced gene is incorporated into the DNA of a plant cell. The DNA of a plant cell includes DNA contained in various organelles (e.g., mitochondria, chloroplasts, etc.) of a plant cell, as well as chromosomes.

The "plant" includes both monocotyledon and dicotyledon. The preferred plant is dicotyledon. The dicotyledon includes both Archichlamiidae and Sympetalidae. A plant of Sympetalidae is preferable. Examples of the plants of Sympetalidae include Gentianales, Solanales, Lamiales, Callitrichales, Plantaginales, Campanulales, Scrophularfales, Rubiales, Dipsacales, Asterales, and the like. A plant of Solanales is preferable. Examples of the plants of Solanales include Solanaceae, Hydrophyllaceae, Polemoniaceae, Cuscutaceae, Convolvulaceae, and the like. Solanaceae is preferable. Solanaceae includes Petunia, Datura, Nicotfana, Solanum, Lycopersicon, Capsicum, Physafis, and Lycium, etc. Plants of Petunia, Datura, and Nicotiana are preferable. Petunia is more preferable. Examples of the plants of Petunia include *P. hybrida, P. axillaris, P. inflata, P. violacea,* and the like. A plant of *P. hybrida* is especially preferable. The "plant" refers to a plant body having a flower and a seed obtained from it, unless otherwise specified. Examples of the "plant cell" include cells from plant organs such as leaves and roots, callus, and suspension cultured cells.

The term "plant expression vector" as used herein refers to a nucleic acid sequence in which various regulatory elements, such as a promotor for, regulating expression of the gene of the present invention, are linked to each other so as to be operable in a host plant cell. Preferably, the plant expression vector may include a plant promoter, a terminator, a drug resistant gene and an enhancer. It is well known to those skilled in the art that a type of the plant expression vector and regulator elements may be varied depending on the type of host cell. A plant expression vector used according to the present invention may further contain a T-DNA region. The T-DNA region allows a gene to be efficiently introduced into plant genome especially when Agrobacterium is used to transform a plant.

The term "plant promoter" as used herein refers to a promoter that functions in a plant. Constitutive promoters as well as tissue-specific promoters which selectively function in a part of a plant body, including a flower, are preferable. Examples of plant promoters include, but are not limited to, Cauliflower mosaic virus (CaMV) 35S promoter and a promoter of nopaline synthase.

The term "terminator" as used herein refers to a sequence positioned downstream of a region of a gene encoding a protein, which is involved in the termination of transcription of mRNA, and the addition of a poly A sequence. The terminator is known to contribute to the stability of mRNA, thereby affecting the expression level of a gene. Examples of such terminators include, but are not limited to, CaMV 35S terminator and a terminator of a nopaline synthase gene (Tnos).

A drug resistant gene is desirable to facilitate the selection of transgenic plants. The examples of such drug resistant genes for use in the invention include, but are not limited to, a neomycin phosphotransferase II (NPTII) gene for conferring kanamycin resistance, and a hygromycin phosphotransferase gene for conferring hygromycin resistance.

An enhancer may be used to enhance the expression level of a gene of interest. As the enhancer, an enhancer region containing a sequence upstream of the above-mentioned CaMV 35S promoter is preferable. More than one enhancers may be used in one plant expression vector.

The plant expression vector according to the present invention may be produced by using a recombinant DNA technique well known to those skilled in the art. The examples of preferable vectors for constructing a plant expression vector include, but are not limited to pBI-type vectors or pUC-type vectors.

A plant expression vector may be introduced into a plant cell by using methods well known to those skilled in the art, for example, a method of infecting a plant cell with Agrobacterium or a method of directly introducing a vector into a cell. The method using Agrobacterium may be performed, for example, as described in Nagel et al., *Microbiol. Lett.,* 67, 325, 1990. According to this method, Agrobacterium is first transformed with a plant expression vector by, for example, electroporation, and then the transformed Agrobacterium is infected to a plant cell by a well-known method such as a leaf-disk method. Examples of the methods for directly introducing a plant expression vector into a cell include, but are not limited to, an electroporation method, a particle gun method, a calcium phosphate method, and a polyethylene glycol method. These methods are well known in the art and a method suitable for a particular plant to be transformed may be suitably selected by those skilled in the art.

The cells in which plant expression vectors have been introduced are selected, for example, based on their drug resistance such as resistance to kanamycin. Thereafter, the cells may be regenerated to a plant body by using a conventional method.

Expression of the introduced gene of the present invention in the regenerated plant body can be confirmed by using a procedure well known to those skilled in the art. This confirmation can be performed by northern blot analysis, for example. More specifically, the total RNAs may be extracted from leaves of a resultant plant, and may be subjected to denatured agarose gel electrophoresis, and then, RNAs may be blotted onto an appropriate membrane. The blot can be hybridized with a labelled RNA probe complementary to a part of the introduced gene to detect mRNA from the gene of the present invention.

The plant of the present invention is a transgenic plant produced by the above-mentioned procedure. It is preferable that the altered characters of the transgenic plant (i.e., morphology of a flower, coloring of a flower, a size of a plant, and/or the number of branches) include that which is not found in a known wild-type or horticultural type. It is also preferable that the altered characters of a plant are horticulturally valuable. Furthermore, it is preferable that altered characters of a flower are stably conserved over subsequent generations.

EXAMPLES

Hereinafter, the present invention will be described by way of the following illustrative examples. Restriction enzymes, plasmids and the like used in the following examples are available from commercial sources.

Example 1

Isolation of PetSPL3 Gene

The protein encoded by the SUPERMAN gene of *Arabidopsis thaliana* was compared with the protein encoded by the GmN479 gene (Kouchi et al., personal communication) expressed specifically in soy bean root nodules. Three different degenerate primers for use in PCR were synthesized based on the amino acid sequences commonly present in both proteins. The nucleotide sequences of two primers oriented 5' to 3' in the genes are 5'-CARGCNYTNGGNGGNCAY-3' (primer 1 (SEQ ID NO: 3), corresponding to an amino acid sequence QALGGH (SEQ ID NO: 8)) and 5'-YTNGGNGGNCAYATGAAY-3' (Primer 2 (SEQ ID NO: 4), corresponding to an amino acid sequence LGGHMN (SEQ ID NO: 9)), respectively, and a nucleotide sequence of a primer oriented 3' to 5' in the genes is 5'-ARNCKNARYTCNARRTC-3[1] (primer 3(SEQ ID NO: 5), corresponding to an amino acid sequence DLELRL (SEQ ID NO: 10)), wherein N is inosine, Y is either C or T, R is either G or A, and K is either T or G.

A first set of PCR was conducted with primer 1 and primer 3 under the following conditions: 94° C. for 10 minute, followed by 30 cycles of 94° C. for 30 seconds, 50° C. for 30 seconds and 72° C. for 60 seconds, and subsequently 72° C. for 7 minutes, using as a template a genomic DNA of a petunia (*Petunia hybrida* var. *Mitchell*) extracted according to the method described in Boutry, M. and Chua N. H.

(1985) EMBO J. 4, 2159–2165. In addition, a second PCR was conducted with primer 2 and primer 3, while using as a template a portion of the product from the first PCR. The reaction conditions were the same as those used in the first PCR. Amplified DNA fragments were inserted into the TA cloning vector (produced by Invitrogen), which were then introduced into *E. col.* according to a conventional method. Plasmids were extracted from the transformed *E. coli* and the nucleotide sequences of the DNA fragment was determined. The results revealed that a part of zinc finger motif contained in common in SUPERMAN and GmN479 was encoded within the resulting DNA fragment. The gene from which this DNA fragment was derived was designated as PetSPL3 gene. In the same series of experiments, the presence of 3 other DNAs (PetSPL1, 2 and 4 genes) containing a nucleotide sequence similar to that of PetSPL3 was demonstrated.

EcoRI—EcoRI fragment was excised from a plasmid containing the PCR-amplified DNA fragment described above. This DNA fragment was labelled with [a-32P]cCTP- using a conventional random prime method (Sambrook et al., (1989) "Molecular Cloning: A LaboratoryManual" (Cold Spring Harbor Laboratory)) to produce a radio labelled probe. Using this labelled probe, a genomic library of petunia (*Petunia hybrida* var. *Mitchell*) which had been generated in a EMBL3 vector (produced by Stratagene) was screened. A clone obtained by this screening contained a genomic DNA fragment of about 3.2kb. This fragment was subcloned into the XbaI site of a pBluescript vector (pBS/PetSPL3). Thus, PetSPL3 gene derived from *Petunia hybrida* was isolated.

Example 2
Analysis of the Nucleotide Sequence and Amino Acid Sequence of PetSPL3 Gene From the pBS/PetSPL3 vector obtained in Example 1, a region containing a protein coding region of the PetSPL3 gene (the region between the HindIII site and the XbaI site) was obtained and further subcloned into a pBluescript vector (pBS/PetSPL3-HX), and then the DNA nucleotide sequence of the protein coding region was determined (SEQ ID NO: 1). From an open reading frame contained in the resulting DNA nucleotide sequence, an amino acid sequence of the protein was deduced (SEQ ID NO: 2).

The comparison of the nucleotide sequences indicated that nucleotide sequence homology of PetSPL3 gene to SUPERMAN, PetSPL1, PetSPL2 and PetSPL4 genes were 29%, 37%, 52% and 23%, respectively. This comparison of the nucleotide sequences was conducted only within the coding region of each gene.

The deduced amino acid sequence of PetSPL3 contained a single TFIIIA-type zinc finger motif similar to that of SUPERMAN. On this basis, it was presumed that-PetSPL3 was a transcription factor. PetSPL1 and PetSPL2, also cloned by the present inventors, showed about 35% homology with SUPERMAN in the full-length amino acid sequences. Whereas, PetSPL3 showed about 20% homology to SUPERMAN in the full-length amino acid sequence.

Further, amino acid homology of PetSPL3 to SUPERMAN in the zinc finger motif was shown to be about 20%, which is lower than those of PetSPL1 and PetSPL2 to SUPERMAN (about 38% and 35%, respectively). Table 1 compares the amino acid sequence of SUPERMAN with that of each PetSPL in the zinc finger motif. Table 1 also shows comparison of C terminal hydrophobic region of SUPERMAN with that of each PetSPL.

TABLE 1

Zinc-finger (SEQ ID NOS:11–15)

| | |
|---|---|
| SUPERMAN | SYTCSFCKREFRSAQALGGHMNVHRRDRARLRLQQSPSSSSTP |
| PetSPL1 | SYTCSFCKREFRSAQALGGHMNVHRRDRARLRL-QSPPRENGT |
| PetSPL2 | SYTCSFCKREFRSAQALGGHMNVHRRDRAILR--QSPPRDINR |
| PetSPL3 | SYECNFCKRGFSNAQALGGHMNIHRKDKAKLKKQKQHQRQQKP |
| PetSPL4 | FYRCSFCKRGFSNAQALGGHMNIHRKDRAKLREISTDNLNIDQ |

C-terminal hydrophobic region (SEQ ID NOS:16–20)

| | *    * *      *      * |
|---|---|
| SUPERMAN | ILRNDEIISLELEIGLINESEQDLDLELRLGFA |
| PetSPL1 | LMKRSEFLRLELGIGMINESKEDLDLELRLGYT |
| PetSPL2 | VIKKSEFLRLDLGIGLISESKEDLDLELRLGST |
| PetSPL3 | GSVDSRENRLPARNQETTPFYAELDLELRLGHE |
| PetSPL4 | CGTLDEKPKRQAENNDMQQDDSKLDLELRLGPD |

From the results described above, it was presumed that PetSPL3 is a novel transcription factor belonging to a class different from those of SUPERMAN, PetSPL1 and PetSPL2. This was also supported by the difference in expression patterns of PetSPL3 and SUPERMAN. See following Example 8.

Example 3
Construction of a Plant Expression Vector Containing a Polynucleotide Encoding the PetSPL3 Gene A DNA fragment (HindIII-XbaI fragment) containing a CaMV 35S promoter in a plasmid pBI221 (purchased from Clontech) and a DNA fragment (SacI-EcoRI fragment) containing a NOS terminator were sequentially inserted into a multicloning site of plasmid pUCAP (van Engelen, F. A. et al., Transgenic Res. 4:288–290 (1995)) to produce pUCAP35S. On the other hand, pBS/PetSPL3-HX plasmid containing PetSPL3 was cleaved at HindIII (position 0) and AccI (position 258) sites. By blunting both the cleaved terminal ends with Klenow enzyme and linking both ends again, a 258bp DNA region upstream of translation initiation site was removed. A DNA fragment (KpnI-SacI fragment) encoding PetSPL3 was excised from the resulting plasmid, and inserted between KpnI and SacI sites of the above described plasmid pUCAP35. This recombinant plasmid was further cleaved with AscI and PacI, and the resulting DNA fragment encoding PetSPL3 was introduced into the AscI and PacI sites of a binary vector pBINPLUS (van Engelen, F. A. et al., (1995), supra).

The constructed high expression vector for PetSPL3 gene (pBIN-35S-PetSPL3) includes, as shown in FIG. 2a, a CaMV 35S promoter region (P35S; 0.9 kb), a polynucleotide of the present invention encoding PetSPL3 (PetSPL3; 0.8 kb) and a terminator region of nopaline synthase (Tnos; 0.3 kb). In FIG. 2, Pnos and NPTII indicate a promoter region of nopaline synthase and neomycin phosphotransferase II gene, respectively. LB and RB indicate T-DNA left border and T-DNA right border, respectively.

Example 4
Introduction of the PetSPL3 Gene into Petunia Cells
(1)(Transformation of *Agrobacterium tumefaciens*)

Agrobacterium tumefaciens LBA4404 line (purchased from Clontech) was cultured in an L medium containing 250 μg/ml streptomycin and 50 μg/ml rifampicin at 28° C. According to the method of Nagel et al. (1990) (supra), a cell suspension of this strain was prepared. The PetSPL3 gene high expression vector constructed in Example 3 was introduced into the above described strain by electroporation.
(2) (Introduction of a Polynucleotide Encoding PetSPL3 into Petunia Cell)

The Agrobacterium tumefaciens LBA4404 line obtained in (1) was cultured (at 28° C., 200 rpm) with agitation in YEB medium (D. M. Glover ed. DNA Cloning, IPL PRESS, second edition, p.78), followed by a 20-fold dilution with sterilized water. Leaf sections of petunia (*Petunia hybrida* var. *Mitchell*) were cultured in this diluted solution. After 2–3 days, the Agrobacterium was removed using a medium containing carbenicillin, and thereafter these leaf sections were subcultured in a selection medium by transferring to new media every 2 weeks. The Kanamycin resistance trait conferred by the expression of the NPTII gene derived from pBINPLUS, introduced together with the above-mentioned PetSPL3 gene, was used as an indicator to select transformed petunia cells. Callus was induced from the transformed cells using a conventional method, and then re-differentiated into a plant body.

Example 5
Expression of the PetSPL3 Gene in a PetSPL3 Transformant Plant

Figure 3:
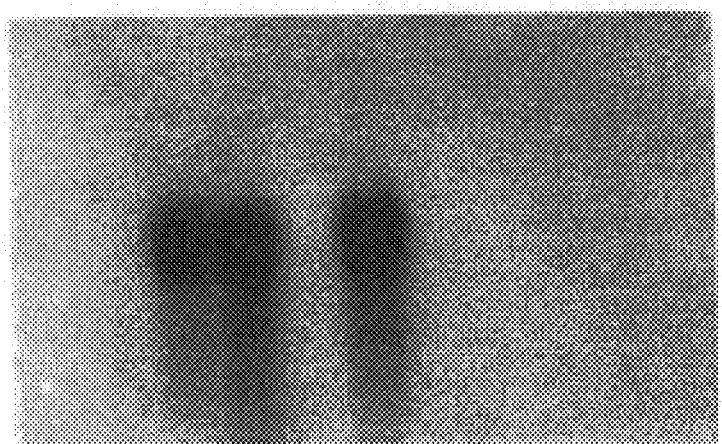
FIG. 3 shows an autoradiogram of a denatured agarose gel electrophoresis image detecting mRNA of PetSPL3 gene in *Petunia hybrida* transformed with the PetSPL3 gene.

Total RNAs were extracted from leaves of 14 PetSPL3 transformed petunias obtained in Example 4. 10 μg each of the extracts was subjected to denatured agarose gel electrophoresis, and blotted onto a Genescreen plus filter (produced by DuPont) in accordance with a conventional method. A PetSPL3 antisense RNA was labelled using DIG RNA labelling kit (produced by Boeringer Mannheim). Hybridization and filter washing were performed with the labelled RNA according to the instructions of the kit. After the washing, the filter was exposed to an XAR film (produced by Kodak) for 1 hour at room temperature. FIG. 3 shows an autoradiogram of an image of denatured agarose gel electrophoresis in which PetSPL3 gene mRNAs were detected for 9 out of 14 petunias. These results indicated that 3 out of 14 individual transformant petunias expressed PetSPL3 mRNA at a high level under the control of a high expression promoter.

Figure 4:
FIG. 4 shows pictures of morphology of a plant body of wild-type *Petunia hybrida* (left) and that of *Petunia hybrida* transformed with the PetSPL3 gene (right).
Figure 5:
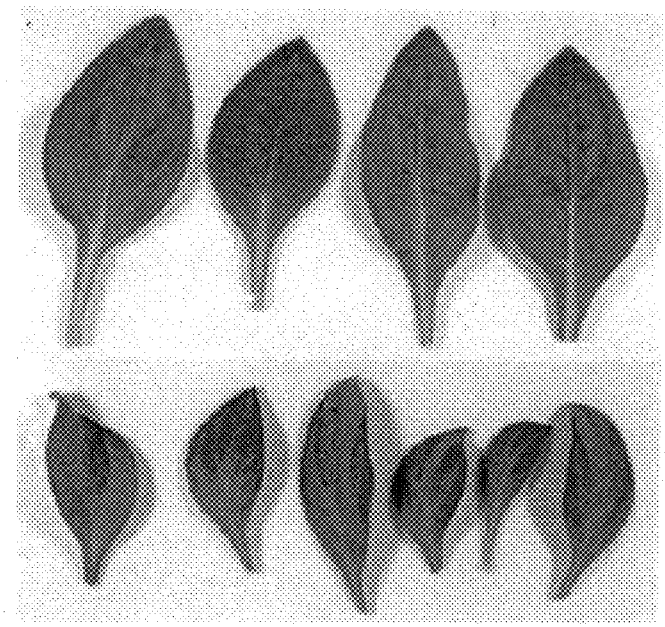
FIG. 5 shows pictures of morphology of leaves of wild-type *Petunia hybrida* (upper part) and those of *Petunia hybrida* transformed with the PetSPL3 gene (lower part).
Figure 6A:
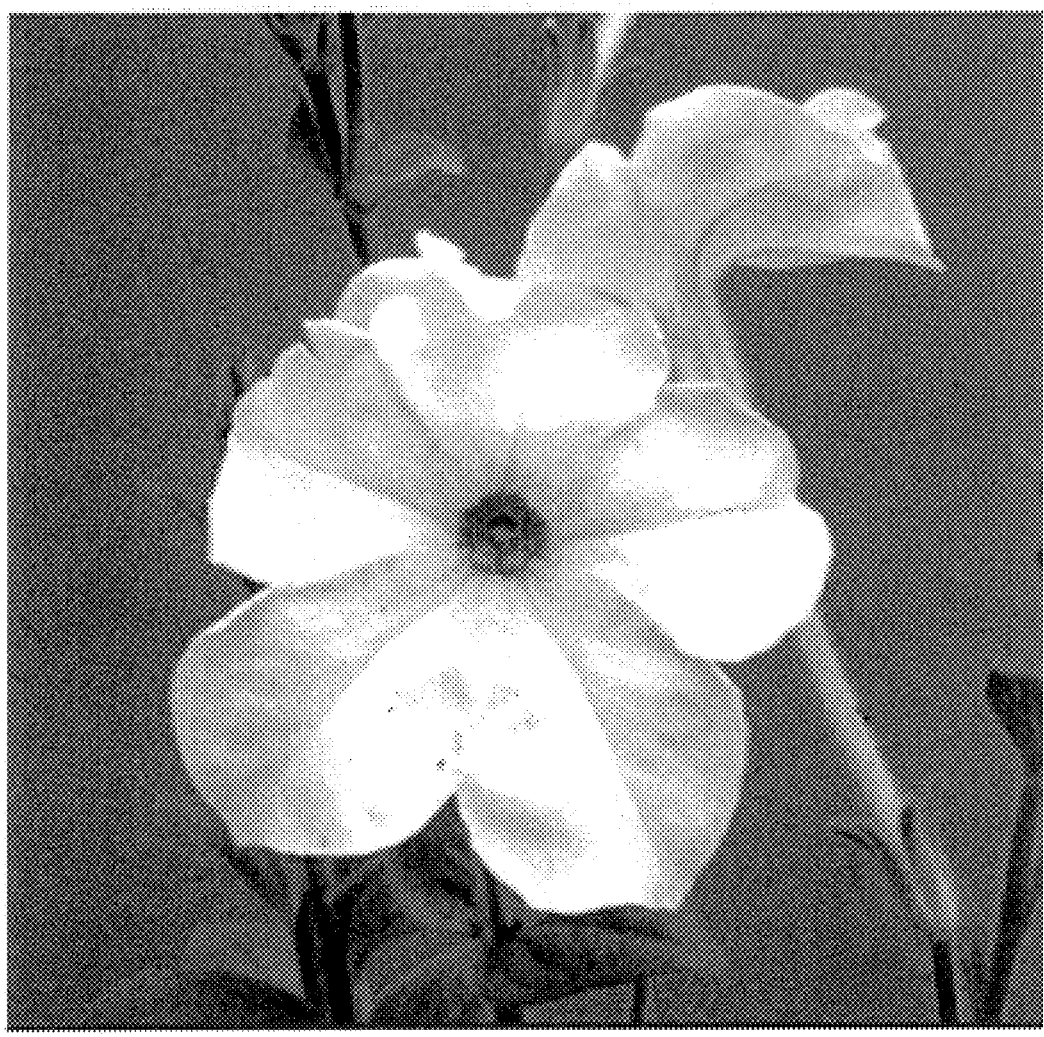
FIG. 6A shows a picture of morphology of a flower of wild-type *Petunia hybrida.
Figure 6B:
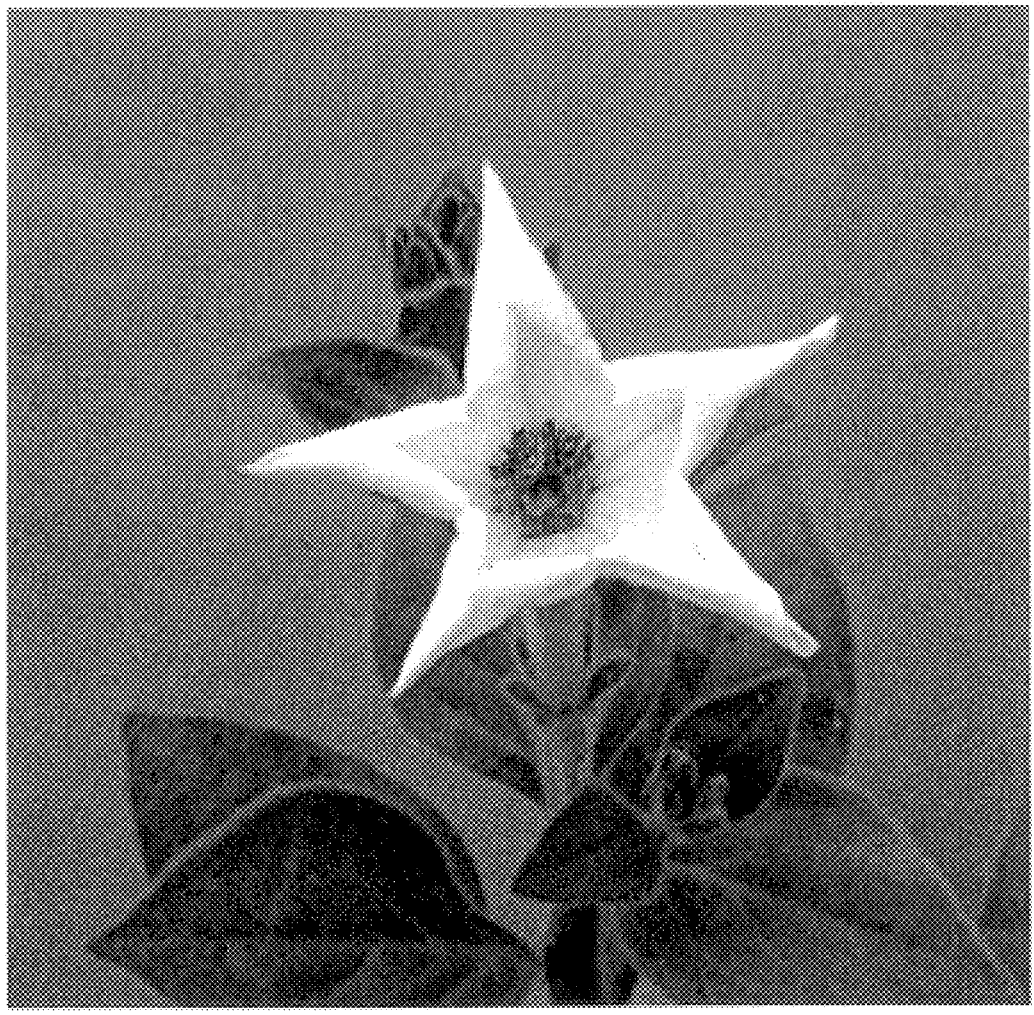
* and FIGS. 6B and 6C show pictures of morphology of flowers of *Petunia hybrida* transformed with the PetSPL3 gene.
Figure 6C:
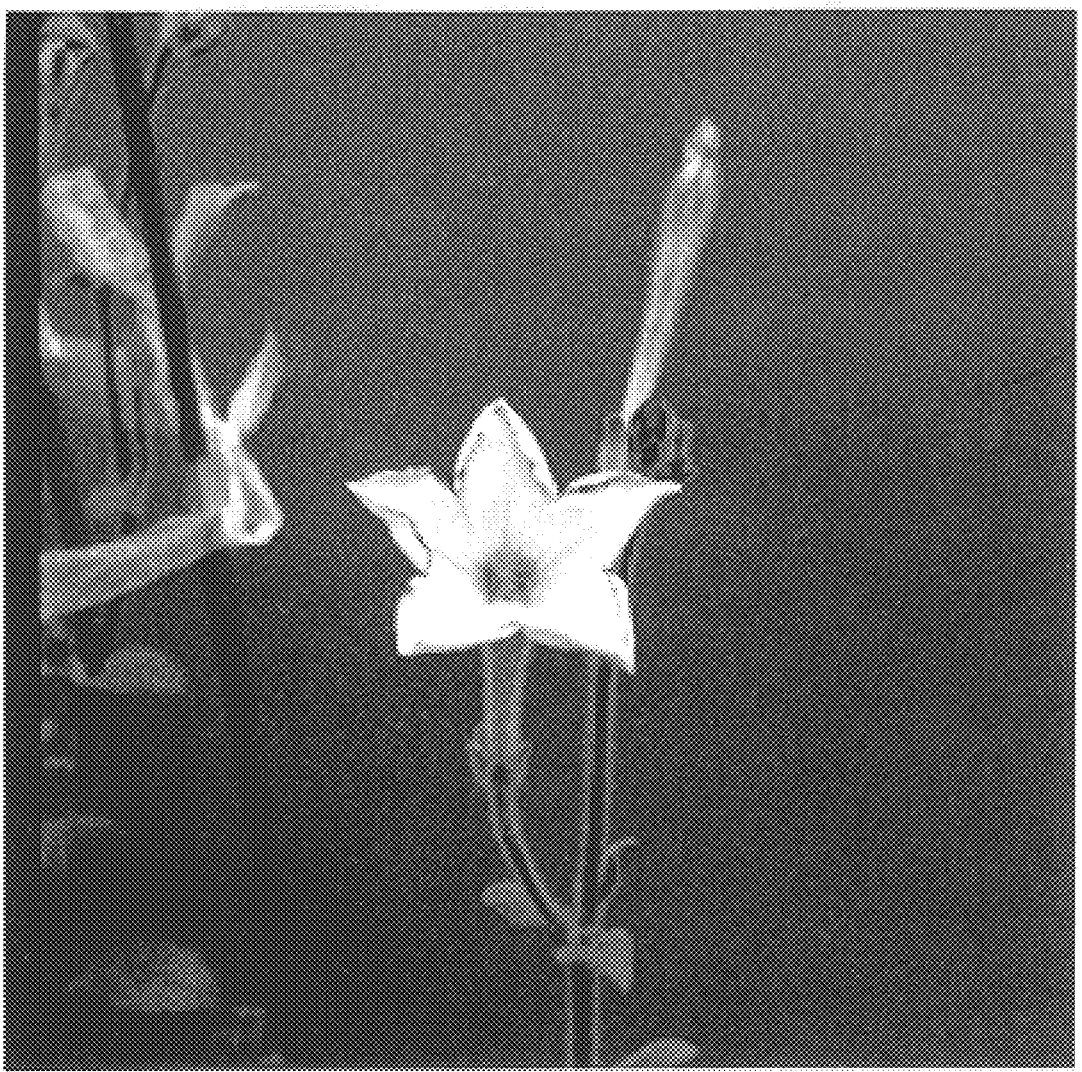

Example 6
Phenotypes of a Transformant Petunia Expressing PetSPL3 Gene at High Level The following phenotypes were commonly observed in 3 individual transformant petunias expressing the PetSPL3 gene at high levels. First, as an observed change in a plant body, significant branching occured with dwarfism of the plant, as a result of reduction of apical dominance (FIG. 4; left panel shows a wild type petunia and right panel shows a PetSPL3-transformant petunia). Leaves became smaller and violet stains presumably resulted from the deposition of anthocyanin pigments were observed over the entire surface (FIG. 5; upper panel shows a leaf of a wild type petunia and lower panel shows a leaf of a PetSPL3-transformant petunia). With respect to flowers, a top view of the wild type flower shows approximatly a round shape, while that of PetSPL3 transformant appeared star shaped (FIG. 6; (*a*): wild type petunia flower, (*b*) and (*c*): PetSPL3-transformant petunia flower). This is presumed to be the result of abnormality in expansion of petals. Mitchell, the variety of Petunia used in the present experiment, has white petals. This has been explained to be the result of mutation in a regulatory gene, such as an2, which controls coloring of petals (Quattrocchio, F., Ph.D. thesis in Amsterdam Free University (1994)). In contrast, in PetSPL3-transformant petunias, pale violet coloring appeared only around the outer edge of petals (FIG. 6(*c*)).

The results described above revealed that morphology and/or coloring pattern of the flower of the PetSPL3-transformant petunia are not found at all or are extremely rarely found in wild-type and horticultural species of *Petunia hybrida*. To the extent the present inventors are aware, there has been no reported examples that such characteristics are conferred to a plant flower by means of genetic engineering. In addition, the PetSPL3-transformant petunia is a dwarf and has increased branching. These characteristics are horticulturally highly useful.

Example 7
Construction of a Promoter Analysis Vector Containing a Polynucleotide from a 5' Upstream Region of PetSPL3 Gene in the Upstream of GUS Reporter Gene In Examples 7 and 8, the promoter activity of the PetSPL3 gene conferring its expression patterns was analyzed, and compared with those of the SUPERMAN gene and the other PetSPL genes.

Figure 2B:
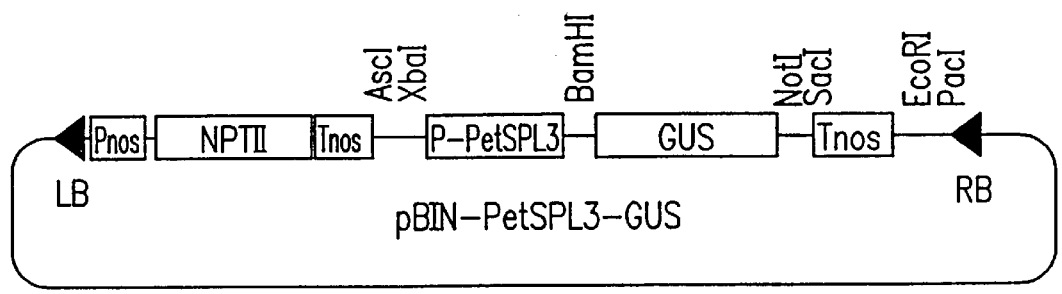
FIG. 2B is a schematic view showing a vector (pBIN-PetSPL3-GUS) for analyzing the promoter of the PetSPL3 gene.

A primer containing a sequence present about 70 bp upstream of the translation initiation site of the PetSPL3 gene, and a BamHI recognition sequence (ACTGGATCCCATTAGAGAGAGAGAG; SEQ ID NO: 6), and an M13 reverse primer (GGAAACAGCTATGACCATG: SEQ ID NO: 7) corresponding to a sequence within a vector were used to conduct PCR using the above described plasmid pBS/PetSPL3 as a template, whereby amplifying a DNA fragment of about 2.4 kb which is believed to contain the promoter region of the PetSPL3 gene. This DNA fragment was cleaved at XbaI and BamHI sites present close to both ends of the fragment. A XbaI-EcoRI fragment containing a β-glucuronidase (GUS) coding region and a terminator of nopaline synthase gene excised from pBI221 (purchased from Clontech) were inserted between XbaI and EcoRI sites of pUCAP (van Engelen, F. A. et al., (1995), supra) to obtain a pUCAPGUS plasmid. The XbaI-BamHI fragment obtained above were inserted upstream (i.e., XbaI and BamHI sites) of the GUS coding region within the pUCAPGUS plasmid. From the resulting plasmid, a DNA fragment containing the 5' upstream region of PetSPL3 gene, the GUS coding region and the terminator region of nopaline synthase was excised with AscI and PacI, and inserted into AscI and PacI sites of pBINPLUS used in Example 3. The thus constructed plasmid for promoter analysis (pBIN-PetSPL3-GUS) is shown in FIG. 2*b*.

Example 8
Expression Pattern of the PetSPL3 Gene in a Stem

Figure 7:
FIG. 7 is a picture showing a GUS-staining pattern of a stem of *Petunia hybrida* transformed with pB-PetSPL3-GUS.

The above-mentioned recombinant plasmid containing a polynucleotide from the 5' upstream region of the PetSPL3 gene upstream of the GUS reporter gene was introduced into petunia (*Petunia hybrida* var. *Mitchell*) in the same manner as in Example 3. Distribution of GUS activity was investigated in a young stem of the resulting transformant using X-GUS as a substrate in accordance with a conventional method (Murakami and Ohashi, Plant Cell Engineering, 14, 281–286, (1992)). As a result, GUS activity was detected specifically at leaf axils (See FIG. 7), indicating that the DNA region containing the 5' upstream portion of the PetSPL3 gene has promoter activity specific to the leaf axil cells. Thus, it was presumed that the PetSPL3 gene was expressed specifically in the leaf axil. This expression specificity is totally different from that of the SUPERMAN gene, which is specific for primordia of stamen and ovule. Taking this difference and a low similarity of amino acid sequences (Example 2) into account, it is concluded that PetSPL3 is a novel transcription factor belonging to a class different from that of SUPERMAN.

According to the present invention, a gene encoding a transcription factor capable of altering morphology, color and the like of a plant is provided. By utilizing the present gene, a plant with altered character can be produced. The generated plant is horticulturally useful because it is provided with the character which is not found or rarely found in a wild-type and a horticultural type.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. An isolated nucleic acid molecule having the nucleotide sequence from the 90th position to the 728th position of the nucleotide sequence represented in SEQ ID NO: 1 of the Sequence Listing.

2. A method for producing a transgenic plant, comprising the steps of:
   introducing the nucleic acid molecule of claim 1 into a plant cell; and
   regenerating the plant cell into a transgenic plant.

3. A method according to claim 2, wherein the plant is a dicotyledon.

4. A method according to claim 3, wherein the plant is a member of the Solanaceae family.

5. A method according to claim 4, wherein the plant is a member of the Petunia genus.

6. A method according to claim 2, wherein the nucleic acid molecule is incorporated into a plant expression vector.

7. A transgenic plant produced by the method of claim 2.

8. A method for altering characters of a plant, comprising steps of:
   introducing the nucleic acid molecule of claim 1 into a plant cell;
   regenerating the plant cell into a transgenic plant; and
   evaluating the change of the characters by comparing the characters of a plant obtained by introducing the nucleic acid molecule with the characters of a plant before introducing the nucleic acid molecule,
   wherein the characters of a plant are selected from the group consisting of the morphology of a flower, the color of a flower, the size of a plant, and the number of branches.

9. An isolated nucleic acid molecule encoding a transcription factor having the amino acid sequence from the 1st position to the 213th position of the amino acid sequence represented in SEQ ID NO: 2, wherein said transcription factor has the functional activity of the amino acid sequence represented in SEQ ID NO: 2.

10. A method for producing a transgenic plant, comprising the steps of:
    introducing the nucleic acid molecule of claim 9 into a plant cell; and
    regenerating the plant cell into a transgenic plant.

11. A method according to claim 10, wherein the plant is a dicotyledon.

12. A method according to claim 11, wherein the plant is a member of the Solanaceae family.

13. A method according to claim 12, wherein the plant is a member of the Petunia genus.

14. A method according to claim 10, wherein the nucleic acid molecule is incorporated into a plant expression vector.

15. A transgenic plant produced by the method of claim 10.

16. A method for altering characters of a plant, comprising steps of:
    introducing the nucleic acid molecule of claim 9 into a plant cell;
    regenerating the plant cell into a transgenic plant; and
    evaluating the change of the characters by comparing the characters of a plant obtained by introducing the nucleic acid molecule with the characters of a plant before introducing the nucleic acid molecule,
    wherein the characters of a plant are selected from the group consisting of the morphology of a flower, the color of a flower, the size of a plant, and the number of branches.

* * * * *